United States Patent [19]
Ganshorn

[11] Patent Number: 5,305,763
[45] Date of Patent: Apr. 26, 1994

[54] EXPIRATORY AIR RECEPTION VESSEL

[76] Inventor: Peter Ganshorn, Goldgrund 5, 8732 Münnerstadt, Fed. Rep. of Germany

[21] Appl. No.: 741,497

[22] PCT Filed: Feb. 3, 1990

[86] PCT No.: PCT/DE90/00075
§ 371 Date: Aug. 1, 1991
§ 102(e) Date: Aug. 1, 1991

[87] PCT Pub. No.: WO90/08504
PCT Pub. Date: Aug. 9, 1990

[30] Foreign Application Priority Data
Feb. 4, 1989 [DE] Fed. Rep. of Germany ........ 3903370

[51] Int. Cl.$^5$ .............................................. A61B 5/091
[52] U.S. Cl. ...................................... 128/730; 128/719
[58] Field of Search ............... 128/719, 725, 727, 728, 128/730; 73/864.62, 864.63; 482/13

[56] References Cited

U.S. PATENT DOCUMENTS

| | | | |
|---|---|---|---|
| 3,669,097 | 6/1972 | Fitz | 128/728 X |
| 3,754,546 | 8/1973 | Cooper | 482/13 |
| 3,793,888 | 2/1974 | Rosenwald | 73/864.62 |
| 4,947,860 | 8/1990 | Fisher | 128/719 |

FOREIGN PATENT DOCUMENTS 630982 12/1927 France .

*Primary Examiner*—Lee S. Cohen
*Assistant Examiner*—Samuel Gilbert
*Attorney, Agent, or Firm*—Edwin D. Schindler

[57] ABSTRACT

A vessel is disclosed for receiving exhaled air in order to measure lung function. The vessel includes a container with two facing inlets which admit exhaled air alternatively. The container houses: either a piston which can slide in the direction of the inlets, and switches which are actuated when the position reaches the wall of the container, whereupon air is admitted through the other inlet; or, two contiguous bags to each of which air is admitted by one inlet so that they move alternately, and a switch which when actuated causes air to be admitted through the other inlet.

10 Claims, 2 Drawing Sheets

EXPIRATORY AIR RECEPTION VESSEL

BACKGROUND OF THE INVENTION

1. Technical Field of the Invention

The invention concerns an expiratory air reception vessel for the measurement of lung function having an inlet.

2. Description of the Prior Art

In order to determine the performance and/or detect diseases of the lung, it is known how to record and at the same time analyze the volume and composition of the expired air from a test person under conditions of changing levels of physical exertion. Of particular interest are the respective proportions of oxygen and carbon dioxide. The concentration of the expired air is subject to fluctuations caused by changes in levels of exertion, and these should be recorded and indicated as soon as possible. These requirements are met by mass spectrometers, which, however, are enormously expensive and costly to procure and maintain. For this reason, expiratory air is, at the moment, fed into a bag with an outlet, so that part of the air found therein can escape and an overloading can be safely ruled out. A part of the air collected is removed and undergoes analysis as regards its composition. Here the disadvantage is that with a changing concentration of expired air, due to the immediate loss and the large volume of this air, the composition in the bag only changes very slowly. The time constant for the measurement of changes in the concentration of the air taken from the bag with the aid of a gas analyzer is therefore considerable. Moreover, it would be desirable if the volume of expired air could be determined.

SUMMARY OF THE INVENTION

On this basis, it is the object of this invention to provide an expiratory air reception vessel that possesses a short response time, is of simple construction and which, in addition, makes it possible to measure the volume of expired air.

In accordance with this invention, this task is solved by means of two inlets disposed opposite each other in a closed container, which can admit expired air alternatively, whereby the container comprises a piston disposed inside, which is movable in a direction towards the inlets, as well as switches, which are operated when the piston reaches the wall of the container, whereby the inlet to be pressurized is changed.

Utilization is in the usual way, i.e. the expired air from the test person is fed from the mouth piece to the inlet and enters the interior of the closed container. In accordance with the concept of the invention, only one single inlet is ever pressurized. As a result, an overpressure arises in the space defined by piston, corresponding wall of the container and inlet pressurized at that moment, causing the piston to move towards the inlet opposite, where, upon reaching the corresponding wall surrounding the inlet, it operates a switch. Consequently, a change in pressurization of the two inlets is achieved, i.e. the expiratory air supplied from now on moves the piston in the opposite direction and it presses the air there outwards. The piston support shall be, as far as possible, friction-free, so that the resistance to be overcome by the expired air remains low and natural conditions prevail during expiration. Because of the geometry of the receptacle, an exact determinable volume and thus volume of air expired is defined. As a rule, dimensioning will be such that several expiration processes fill the whole volume. An average of the gas concentration is formed during the course of several expiration processes. When the volume built up is eventually is emptied by means of a return movement of the piston, a part of the gas mixture there can be removed and supplied to a gas analyzer. One measures the mean value during the course of several expiration processes.

As a decisive advantage can be seen, firstly, that the measured volume is always constant and changes in the composition of the expiratory air can be recorded and undergo analysis relatively rapidly, since the reversal in the direction of the movement of the piston builds up a gas volume fully new in composition; the mean being taken during the course of several expiratory processes, following which the gas volume is fed away to undergo analysis. One of the central ideas of this invention includes the use of relatively simple and inexpensive analysis equipment. A further advantage of the invention is to allow the quickest possible assimilation and tracking of changes in the gas concentration. Compared with the prior art, the device according to this invention, does not require any costly analysis equipment and nevertheless allows a comparatively substantial increase in the speed of data collection and tracking of changes in the concentration of the expired air.

Independent of the expiratory air reception vessel described thus far, a further solution of the task according to this invention is proposed and is characterized by a container having openings, in which two inlets are found that admit expiratory air alternatively, whereby the container comprises two bags disposed adjacent to each other, which can be pressurized by means of one of the respective inlets, hereby moving towards one another, as well as a switch that changes the inlet pressurized when operated.

The device defined above, which is widely similar in function to the device described before, is different though as regards the construction found inside of the container. Instead of having a movable piston, two bags are disposed inside adjacent to each other, which can be pressurized by means of one of the respective inlets.

During pressurization, one of the bags expands in volume, which causes the air found in the other bag to be pressed out. Only when the whole bag fills the interior of the container—less the natural volume of the other bag, does one achieve what is defined as a volume. Through a change in pressurization, the volume of opposing bag expands and the air in the first bag is released outwards. As regards function, the walls of bags, which are adjacent to each other, assume the function of the piston moving back and forth in the embodiment described previously. Here, one of the decisive advantages lies in the possibility of a comparatively inexpensive manufacture. The walls of the container must be provided with openings, in order to allow the bag unrestricted movement.

Otherwise, there is wide similarity with the first solution named as regards function and advantages achievable. The expiratory air reception vessels described thus far having only two inlets far must necessarily have provisions that allow the inlet momentarily not in use to come into contact with atmosphere, in order to facilitate the escape of air. The use of corresponding valves is conceivable here, would result, however, in the creation of an additional flow resistance, which has the disadvantage of increasing the pressure required to move the bag/piston and therefore also expiratory resistance. A possible structural solution includes the attachment of an outlet with a large cross section for the escaping air. In addition and independent thereof, a removal opening can be provided serving the extraction of gas samples or the connection to a gas analyzer. A possible further opening can be used to return gas volumes which may have been removed.

The change in the pressurization of the two inlets in a manner controllable by switches is achieved preferably by means of branching the tube leading from the mouth piece at a point provided with a 2-way valve and from there leading to one of the respective inlets. Controlled by means of switches, the 2-way valve pressurizes only one of the inlets with expiratory air at any one time.

Mechanical or electromechanical structures can be used as switches. In view of soft-touch operation and avoidance of any possible resistances, it is recommended that photoelectric barriers be used, which allow a non-contact operation of the switch. They can also be used, however, as indicators for certain (discrete) positions of the piston or bags.

In an advantageous embodiment, a differential-pressure transformer is used, which registers the pressure formed by the bags or piston in both of the chambers at the same time and operates the corresponding switch, causing a change in pressurization.

In the case of movements in a direction not corresponding with the horizontal line, a component of gravity causes an acceleration in a downward direction. In order to stop this leading to a falsification of the measurement results, special compensatory provisions must be made. To avoid such effects and to guarantee as simple and therefore inexpensive construction as possible, it is advantageous to align the movement of the piston or bag on the horizontal line.

Following a certain period of use, a collection of moisture contained in breath within the reception vessel is unavoidable. In order to collect and remove this, it is advantageous to attach a water trap to the bottom side, i.e. where the moisture is primarily deposited.

BRIEF DESCRIPTION OF THE DRAWING FIGURES

Further details, features and advantages of the invention can be taken from the following description part, in which a typical embodiment of the invention is explained in greater detail with the aid of the drawing. It shows:

FIG. 1 an embodiment with movable pistons in the container; and

FIG. 2 a container with two bags disposed therein.

DETAILED DESCRIPTION OF THE DRAWING FIGURES

Figure 1:
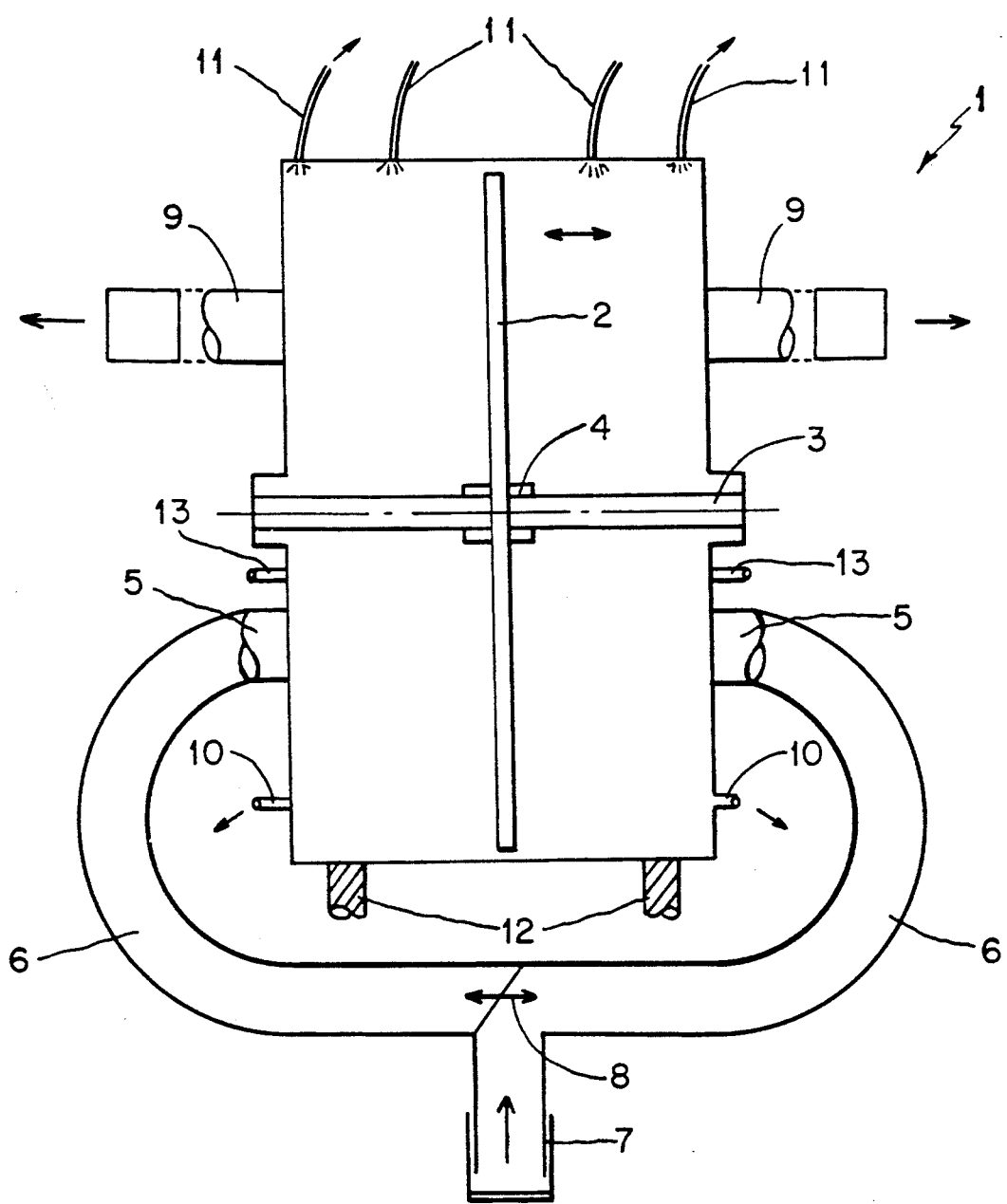

In container (1) is a piston (2), which is mounted upon a centrally disposed rail (3) aided by support (4). In order to make the residual volume zero upon reaching the reversal point, the side wall has been formed to correspond with the contours of piston (2) and support (4).

On the right as well as the left side, container (1) is provided with an inlet (5), where a tube (6), which starts at mouth piece (7), ends, whereby said tube branches at a point provided with a 2-way-valve (8) and is fed from there to the two inlets (5). The expiratory air received by means of the mouth piece (7) is fed via the 2-way-valve (8) to one of the inlets (5).

In addition, in container (1), on the sides respective to the inlets (5), there is an outlet (9), which allows air to escape and through which the escaping air is released outwards, as well as a removal opening (10), which allows gas samples to be taken, as well as a return opening (13). To this, a gas analyzer can be directly connected.

The 2-way valve (8) is operated by means of switch (11) which determines the movement of piston (2).

On the bottom side are disposed two water traps (12), which serve the collection of moisture contained in the expired air.

The function is as follows: The test person provides expiratory air via mouth piece (7), the supply of which passes through one of the inlets (5) and is determined by 2-way valve (8). From there it reaches the interior of the space defined by piston (2) and the corresponding walls of container (1), whereby outlet (9) as well as removal opening (10) are closed, so that a pressure is built up which lies above that of the chamber opposite, so that piston (2) moves towards the wall of container (1) opposite to the pressurized inlet (5). The air collected there is released outwards via the opened outlet (9). By means of the appropriate removal opening (10), gas samples, to undergo analysis, are extracted.

Upon reaching the facing wall, switch (11) is operated, 2-way valve (8) switched and inlet (5), thus far not used, supplied with expiratory air, outlet (9) on this side and possibly removal opening (10) closed, and opposing outlet (9) opened, resulting in a movement of piston (2) in the opposite direction. The process described above reverses.

The aim and object of the device according to this invention is to carry out an averaging process during the course of several expiratory actions in a way and manner as simple as possible and, further to provide a gas sample, for the analysis of which inexpensive equipment with comparatively high time constants is suitable and utilizable. On the other hand, it is to be assured that changes in the gas concentration are recorded exactly and tracked in a suitably rapid time, i.e. within a certain period of time determined by the volume of the reception vessel.

Figure 2:
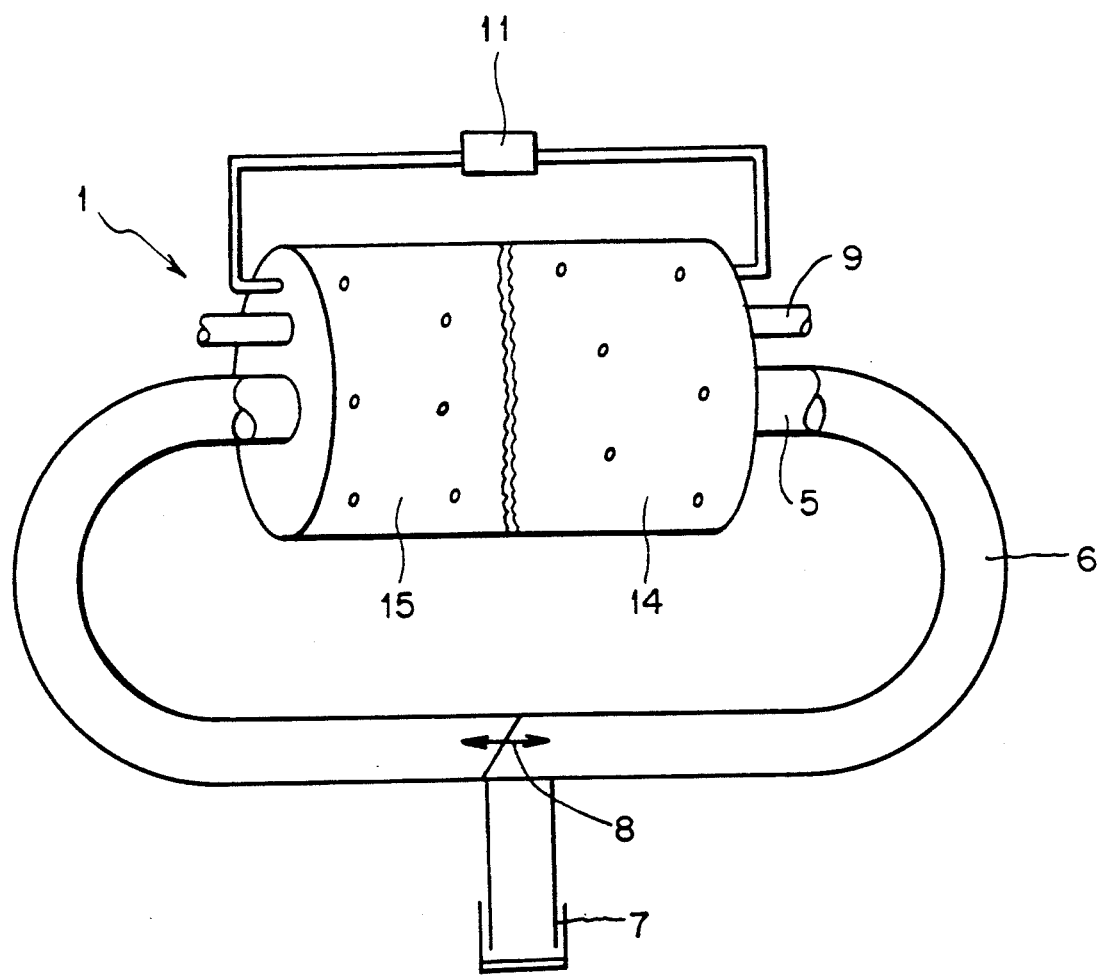

FIG. 2 also shows a container (1), in the interior of which, however, instead of the piston, two bags (14), (15) are disposed, these being arranged such that their respective bottoms rest adjacent to each other. By means of one of the respective inlets (5), one of the two bags (14), (15) is pressurized alternatively. Furthermore, there is an outlet (9), which is provided with a valve. Pressurization of one of the bags causes its volume to expand, at the same time the other bag is displaced until the interior of the container is completely filled. This defines the recorded volume. Following this, the operation is switched to the other bag and the process starts anew on the other side. The volume of the bag is changed by folding it together and/or by elastic extension of the wall.

Pressurization is controlled by means of 2-way valve (8) already described above, said 2-way valve being controlled furthermore by a differential-pressure transformer. To achieve this, the pressure inside each of bags (14), (15) is measured, compared and used to switch valve (8).

Container (1) is provided with openings, which guarantee an unimpeded unfolding of bags (14), (15) inside.

I claim:

1. An expiratory air reception vessel for a measurement of lung function, comprising:

a closed container having two inlets, said two inlets being disposed opposite to one another and able to be pressurized alternatively with expired air from a patient; switching means for changing an inlet of said two inlets which is pressurized at any given time; and a piston means disposed within said closed container for operating said switching means, said piston means being movable within said container in a direction toward one of the two inlets wherein said one of said two inlets not pressurized at any given time is in contact with the atmosphere.

2. The expiratory air reception vessel according to claim 1, wherein said closed container includes an outlet, or removal opening, and a return opening for a return of a removed gas volume, said outlet or removal opening, and said return opening are disposed next to one of said inlets.

3. The expiratory air reception vessel according to claim 1, further comprising a mouth piece and a two-way valve with a tube wherein said mouth piece is connected by means of said two-way valve with said tube, which leads to outlets of said closed container.

4. The expiratory air reception vessel according to claim 1, wherein said switching means is a photoelectric barrier and serves as an indicator of discrete positions of said piston means.

5. The expiratory air reception vessel according to claim 1, further comprising a water trap which is disposed on a bottom side of said closed container.

6. A expiratory air reception vessel for a measurement of lung function, comprising:

a container having two inlets disposed therein, said two inlets being able to be alternatively pressurized with an expiration of air wherein one of said two inlets not pressurized at any given time is in contact with the atmosphere;

two bags disposed adjacent one another within said container, said bags being able to be pressurized by means of one of said two inlets thereby causing said bags to be moved toward one another; and, switching means for changing an inlet of said two inlets being pressurized when said container is completely filled, said switching means being operable by said bags.

7. The expiratory air reception vessel according to claim 6, wherein said container includes an outlet, or removal opening, and a return opening for a return of a removed gas volume, said outlet or removal opening, and said return opening are disposed next to one of said inlets.

8. The expiratory air reception vessel according to claim 6, further comprising a mouth piece and a two-way valve with a tube wherein said mouth piece is connected by means of said two-way valve with said tube, which leads to outlets of said closed container.

9. The expiratory air reception vessel according to claim 6, wherein said switching means is a photoelectric barrier and serves as an indicator of discrete positions of said bags.

10. The expiratory air reception vessel according to claim 6, further comprising a water trap which is disposed on a bottom side of said container.

* * * * *